US 6,695,076 B2

(12) United States Patent
Masui et al.

(10) Patent No.: US 6,695,076 B2
(45) Date of Patent: Feb. 24, 2004

(54) METHOD OF CORING CRUSTAL CORE SAMPLE, AND ANTIMICROBIAL POLYMERIC GEL AND GEL MATERIAL USED IN THE METHOD

(75) Inventors: Noriaki Masui, Kanagawa (JP); Shigeru Deguchi, Kanagawa (JP); Kaoru Tsujii, Kanagawa (JP); Koki Horikoshi, Kanagawa (JP)

(73) Assignee: Japan Marine Science & Technology Center, Yokosuka (JP)

(*) Notice: Subject to any disclaimer, the term of this patent is extended or adjusted under 35 U.S.C. 154(b) by 6 days.

(21) Appl. No.: 10/053,407

(22) Filed: Jan. 18, 2002

(65) Prior Publication Data

US 2002/0139583 A1 Oct. 3, 2002

(30) Foreign Application Priority Data

Jan. 31, 2001 (JP) ......................... 2001-024145

(51) Int. Cl.[7] ............................................... E21B 49/02
(52) U.S. Cl. ........................................... 175/58; 175/20
(58) Field of Search ........................... 175/20, 58, 60, 175/65

(56) References Cited

U.S. PATENT DOCUMENTS

| 3,975,280 A | * 8/1976 | Hachmann et al. ......... 252/102 |
| 5,482,123 A | 1/1996 | Collee ........................ 175/58 |
| 6,164,389 A | * 12/2000 | Fanuel et al. ................. 175/20 |

FOREIGN PATENT DOCUMENTS

JP  6-337378  12/1994

OTHER PUBLICATIONS

T. Ikeda et al, " Biologically active polycations, 4[a)]— Synthesis and antimicrobial activity of poly(trialkylvinyl-benzylammonium chloride)s", *Makromol. Chem.*, vol. 185, pp. 869–876 (1984).

* cited by examiner

*Primary Examiner*—Zakiya Walker
(74) *Attorney, Agent, or Firm*—Frishauf, Holtz, Goodman & Chick, P.C.

(57) ABSTRACT

A method of taking a crustal core sample, wherein the crustal core sample is obtained in a state coated with an antimicrobial polymeric gel formed of a polymer obtained by polymerizing an antimicrobial monomer, preferably a quaternary ammonium salt compound. The polymer preferably contains a component derived from the antimicrobial monomer in a proportion of 1 to 10 mol%.

10 Claims, 4 Drawing Sheets

METHOD OF CORING CRUSTAL CORE SAMPLE, AND ANTIMICROBIAL POLYMERIC GEL AND GEL MATERIAL USED IN THE METHOD

BACKGROUND OF THE INVENTION

1. Field of the Invention

The present invention relates to a method of coring a crustal core sample, which is available to, for example, researches on intracrustal microorganisms in the crustal core, and antimicrobial polymeric gel and a gel material used in this method.

2. Description of the Background Art

In recent years, researches on crustal interiors have been progressed, and a presence of subterranean microorganisms under a depth, high-temperature and high-pressure environments in the crustal interior has been reported. According to researches on intra-crustal microorganisms in a subterranean microbial sphere composed of these subterranean microorganisms, there are important hidden possibilities such as elucidation of influences of material conversion and mass transfer in a deep geological environment for example, and further, elucidation of origin of life on the primitive earth and evolution thereof, or development of drugs and novel materials.

A crustal core sample can be taken with comparative ease from the crust at the depth closer to mantle by drilling crust of sea bed by means of, for example, a drill ship. As an example of a method for conducting the drilling using the drill ship, for example, a riser drilling method has been known. In this method, a drill pipe extending from the drill ship to the sea bed is rotated to drill the crust by means of a drill bit provided on the tip thereof and at the same time, to feed circulating fluid such as drilling mud or sea water, in which the specific gravity, viscosity, chemical composition, etc. have been adjusted according to the condition of the crust drilled, to the drill bit.

A crustal core sample obtained by such a method has a great possibility that the state of the sample present in the crust as it is may be lost by an influence exerted from the outside during the coring operation, for example, by causes such as its contact with the circulating fluid. In such a case, there is a possibility that the crustal core sample obtained may become useless for various research objects.

In order to deal with such a problem, a method in which when a crustal core sample is cored, the surface thereof is coated with non-invasive gel, thereby obtaining the crustal core sample in a state that its physical structure has been protected from the external factor is disclosed in U.S. Pat. No. 5,482,123.

In this method, however, there is a possibility that adventitious heterogeneous microorganisms may permeate the gel coat on the surface of the core sample to enter the interior of the gel coat, thereby adhering to the crustal core sample. The microorganisms adhered, then may possibly grow on the surface or in the interior of the crustal core sample.

In the handling of the gel forming the surface coat, it is extremely difficult to prevent the gel from being contaminated with the microorganisms because the microorganisms unavoidably adhere to the gel itself.

The crustal core sample contaminated with the adventitious heterogeneous microorganisms by the above-described cause or any other cause becomes unsuitable for use in researches on intracrustal microorganisms.

As described above, according to the conventional method for coring a crustal core sample, measures against the microbial contamination by mixing of the adventitious heterogeneous microorganisms or growth thereof are insufficient. Therefore, the crustal core sample taken by such a method involves a problem that the sample is not fully suitable for use in researches on intracrustal microorganisms.

SUMMARY OF THE INVENTION

The present invention has been made on the basis of the foregoing circumstances and has as its object the provision of a method which has no possibility of microbial contamination from the exterior and is capable of obtaining a crustal core sample suitable for use in researches on intracrustal microorganisms.

Another object of the present invention is to provide antimicrobial polymeric gel used in this method and a gel material therefor.

According to the present invention, there is thus provided a method of taking a crustal core sample, comprising drilling the crust, wherein the crustal core sample is taken in a state coated with antimicrobial polymeric gel formed of a polymer obtained by polymerizing an antimicrobial monomer.

In this method, the antimicrobial monomer used for obtaining the polymer forming the antimicrobial polymeric gel may preferably be a quaternary ammonium salt compound, and the quaternary ammonium salt compound may preferably be at least one of an aromatic compound represented by the following general formula (1), an acryloyloxyalkyltrialkylammonium salt compound, a methacryloyloxyalkyltrialkylammonium salt compound, an acryloyloxyalkylpyridinium salt compound and a methacryloyloxyalkylpyridinium salt compound.

General Formula (1):

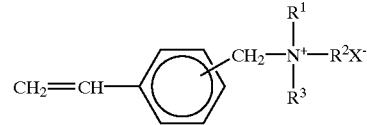

wherein $R^1$ means a linear or branched alkyl group having 1 to 18 carbon atoms, $R^2$ and $R^3$ are methyl groups, and $X^-$ denotes a halogen ion.

Further, the antimicrobial monomer used for obtaining the polymer forming the antimicrobial polymeric gel may also be a phosphonium salt compound. In this case, the phosphonium salt compound may preferably be an aromatic compound represented by the following general formula (2):

General Formula (2):

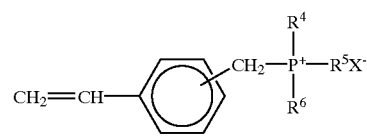

wherein $R^4$, $R^5$ and $R^6$ may be the same or different from one another and independently mean a linear or branched alkyl group having 1 to 18 carbon atoms, and $X^-$ denotes a halogen ion.

The polymer forming the antimicrobial polymeric gel may also preferably contain a component derived from the antimicrobial monomer in a proportion of 1 to 10 mol %.

Further, the polymer forming the antimicrobial polymeric gel may preferably be hydrophilic and be a copolymer obtained from the antimicrobial monomer and at least one of acrylamide, methacrylamide, N,N'-methylenebisacrylamide and N,N'-methylenebismethacrylamide.

According to the present invention, there is also provided an antimicrobial polymeric gel suitable for use in taking a crustal core sample, comprising a polymer obtained by polymerizing an antimicrobial monomer, wherein the gel is used for coating the crustal core sample upon the taking of the crustal core sample by drilling the crust.

According to the present invention, there is further provided a powdered gel material suitable for use in taking a crustal core sample, which forms antimicrobial polymeric gel by adding water thereto, wherein the antimicrobial polymeric gel is used for coating the crustal core sample upon the taking of the crustal core sample by drilling the crust.

According to such a method of taking the crustal core sample as described above, a crustal core taken out of the crust by drilling comes to be taken in a state that the whole thereof has been coated with the antimicrobial polymeric gel, whereby microbial contamination with adventitious microorganisms can be sufficiently and effectively prevented, and the growth of the adventitious microorganisms is inhibited even if the antimicrobial polymeric gel is invaded thereby. In addition, the antimicrobial polymeric gel itself is not contaminated with any microorganisms.

Since the antimicrobial polymeric gel is a polymeric material composed of a polymer, and an antimicrobial component by the antimicrobial monomer forms a part of the molecular structure thereof, the antimicrobial component is prevented from being separated and dissolved out. Accordingly, the crustal core sample obtained is not contaminated with the antimicrobial component, and so the ecological system of said crustal core sample is sufficiently protected, and moreover the antimicrobial activity or antimicrobial performance of the antimicrobial polymeric gel is exhibited stably over a long period of time.

Further, the antimicrobial polymeric gel is hydrophilic, whereby the gel has excellent affinity for the surface of the crustal core sample, and good coating property is hence achieved.

Besides, the powdered gel material suitable for use in taking a crustal core sample permits the provision of the intended antimicrobial polymeric gel with extreme ease, and is light-weight, so that its shipment and storage are extremely easy and convenient from the viewpoint of practical use.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE PREFERRED EMBODIMENTS

The present invention will hereinafter be described in detail.

As an example of a drilling method for taking a crustal core sample, the riser drilling method will be first described by reference to the drawings.

Figure 1:
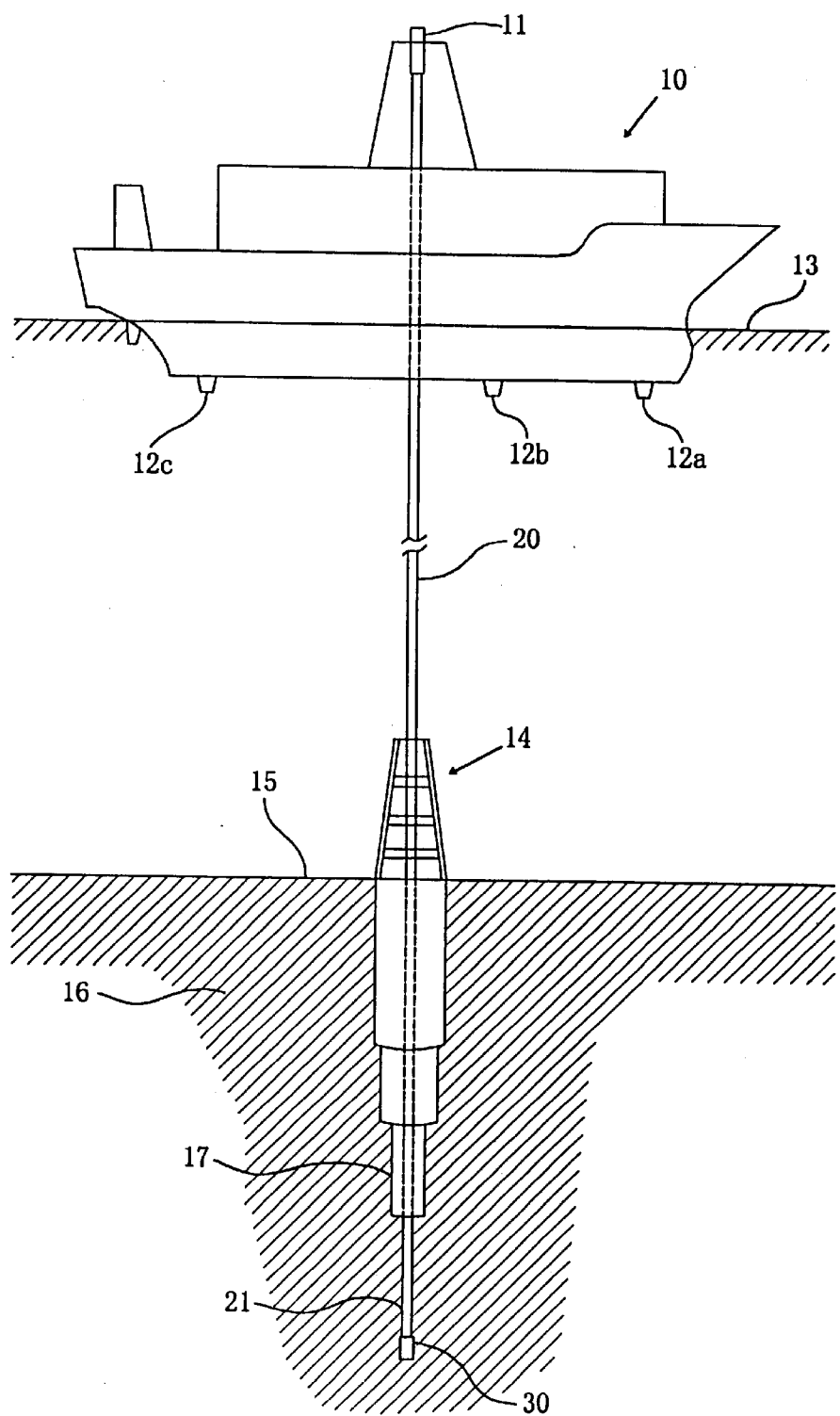
FIG. 1 partly schematically illustrates a state of a coring operation of submarine crust making use of a drill ship.

FIG. 1 illustrates a case where sea bed crust is cored by means of a drill ship in accordance with the riser drilling method.

In this drilling method, a drilling operation is conducted by a riser drilling system provided on a drill ship 10 on the surface 13 of the sea. In the riser drilling system, a riser pipe 20 extending downward from the drill ship 10 into the sea is provided, and a drill pipe 21 is arranged within this riser pipe 20. This drill pipe 21 is so constructed that its upper end is connected to a top drive 11 which is a rotating drive mechanism on the drill ship 10, and its lower part enters the crust 16 through a blowout preventer 14. A drill bit 30 is provided at the lower end of the drill pipe 21.

The drill ship 10 is generally equipped with an automatic ship-position holding system constructed by correlating a plurality of thrusters 12a, 12b and 12c provided on the bottom of the ship, a differential global positioning system (DGPS) making good use of, for example, an artificial satellite, and etc. According to this automatic ship-position holding system, the position of the ship can be held within a region of a small radius with a drill hole in the surface 15 of the sea bottom as the central figure without being affected by the wind and the current even in the open sea.

The drill bit 30 is rotated through the drill pipe 21 by the top drive 11, whereby the crust 16 is drilled from the surface thereof, and the lower end of the drill pipe 21 goes down inside the crust 16. At this time, a circulating fluid composed of drilling mud, sea water or the like is fed to the drill bit 30 through the riser pipe 20. A plurality of casing pipes 17 different in length from each other provided at the lower part of the blowout preventer 14 is inserted according to the depth of the drilling, whereby falling of the wall surface in the drill hole is prevented. Reference numeral 15 indicates the surface (sea bed surface) of the crust.

A number of safety valves for pressure relief are provided in the blowout preventer 14, and the pressure within the drill hole is controlled by these safety valves, whereby rapid blowout of high-pressure hydrocarbon gases, interstitial water within the crust and/or the like is controlled to surely continue a safe drilling process.

Figure 2:
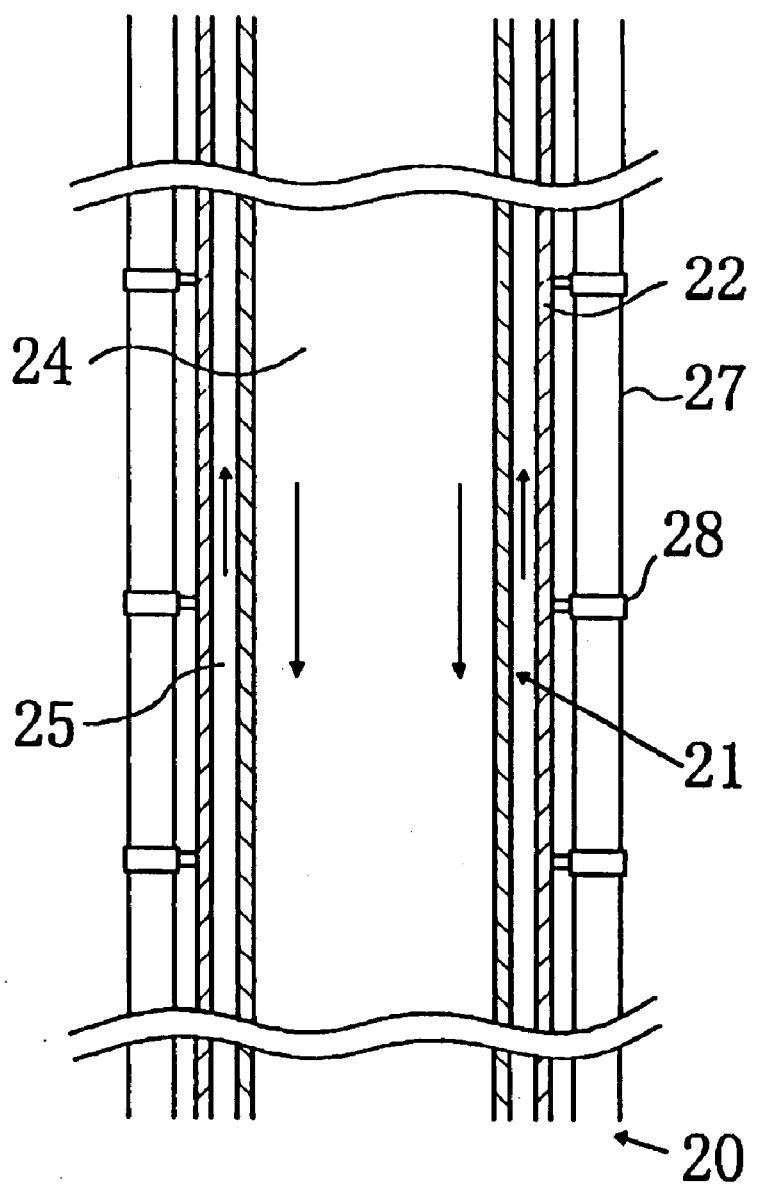
FIG. 2 is a partially sectional view illustrating details of constructional units constructing a riser pipe 20 together with a section of a main pipe 22, through which a drill pipe 21 extends, taken along the axis of the pipe.

FIG. 2 is a sectional view illustrating the construction of the riser pipe 20 in which the drill pipe 21 has been provided.

As illustrated in FIG. 2, the riser pipe 20 is constructed as a double-pipe structure composed of a main pipe 22 and the drill pipe 21 provided in the main pipe 22. Through a flow path 24 within the drill pipe 21, the circulating fluid is fed, and moreover a core sampling system or the like is guided to the drill hole. On the other hand, a circulating flow path, through which the circulating fluid is returned back to the drill ship 10, is defined by an annular flow path 25 formed between the main pipe 22 and the drill pipe 21.

More specifically, the circulating fluid is fed to the drill bit 30, ejected within the drill hole from the tip of the lower part thereof and then circulated through the annular flow path 25. This circulating fluid is a fluid of the specific gravity, viscosity, chemical composition, etc. of which have been adjusted according to, for example, the geology of the crust. As the circulating fluid, for example, that obtained by mixing various substances into drilling mud available in a drilling site may be used.

Incidentally, the necessary lengths of the main pipe 22 and the drill pipe 21, and increases thereof are actually achieved by successively jointing a great number of respective elements thereof to one another as needed. Reference numerals 27 and 28 indicate a kill choke line and a line holder, respectively.

The above-described riser drilling method has such merits as described below, whereby it is a method capable of stably conducting a drilling operation.

(1) Removal of Drill Debris:

Drill debris collected on the bottom of the drill hole is conveyed to the drill ship 10 through the annular flow path 25 by the circulating fluid ejected from the drill bit 30.

(2) Protection and Stabilization of Wall Surface of Drill Hole:

The viscous component in the circulating fluid ejected from the drill bit 30 adheres to the wall surface of the drill hole to form a thin film-like protective film 18 (see FIG. 5), whereby falling of the wall surface in the drill hole is prevented.

The specific gravity in the composition of the circulating fluid is heightened, whereby the equilibration of pressure against the stratum pressure in a deep depth can be conducted, and an effect of preventing a fluid in the stratum from penetrating into the drill hole is brought about.

(3) Cooling and Lubrication of Drill Bit:

The drill bit 30 is cooled by contact of the circulating fluid with its surface to prevent it from being excessively heated by gradually rising crustal heat, and lubricating action is achieved between the drill bit 30 and the crust, so that the degree of friction in the drill bit 30 is lowered to lessen the abrasion of the drill bit 30.

(4) The constitutive substances and the like of the drill debris contained in the circulating fluid sent to the drill ship 10 are successively analyzed and monitored, whereby the geological condition of the crust, to which drilling is being conducted at this very moment, is easy to be always confirmed and grasped.

As understood from the above fact, the drill pipe 21 and drill bit 30 for drilling the crust 16 are required to permit feeding and ejecting the circulating fluid from the tip parts thereof, and the so-called coring drill bit having an opening at the central part along the rotating axis thereof is preferably used.

As specific examples of a core sampling system actually used, may be mentioned those having, as an inner barrel, a standard rotary core barrel (RCB), a hydraulic piston core barrel (HPCB), a motor-driven core barrel (MDCB), a pressure core barrel (PCB) or the like. These are used properly according the geological condition of the crust.

The method of coring a crustal core sample according to the present invention will hereinafter be described specifically in the case where it is practiced in accordance with the riser drilling method making good use of the standard rotary core barrel (RCB).

Figure 3:
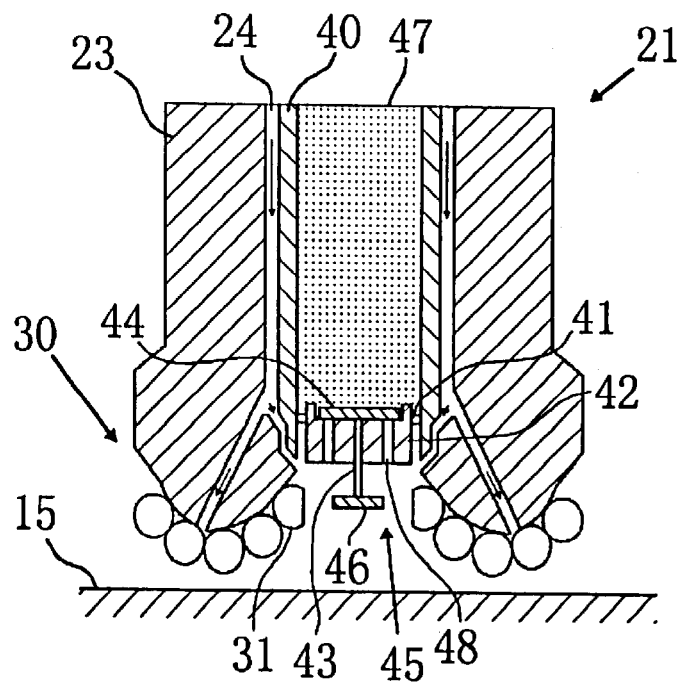
FIG. 3 is a sectional view illustrating a drill pipe and a drill bit right before a drilling of sea bed is started, with the section taken along the axis of the pipe partly schematically shown.
Figure 4:
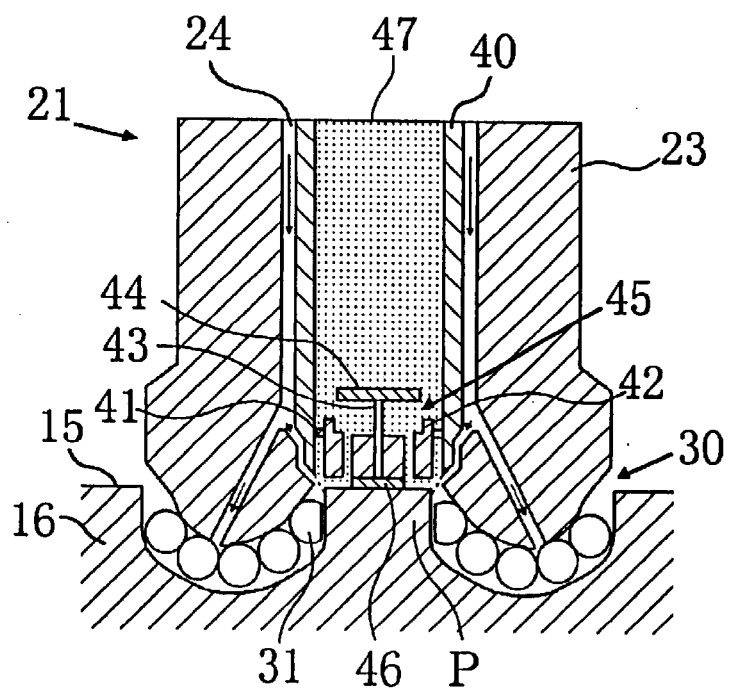
FIG. 4 is a sectional view illustrating the drill pipe and the drill bit right after a drilling of sea bed is started, with the section taken along the axis of the pipe partly schematically shown.
Figure 5:
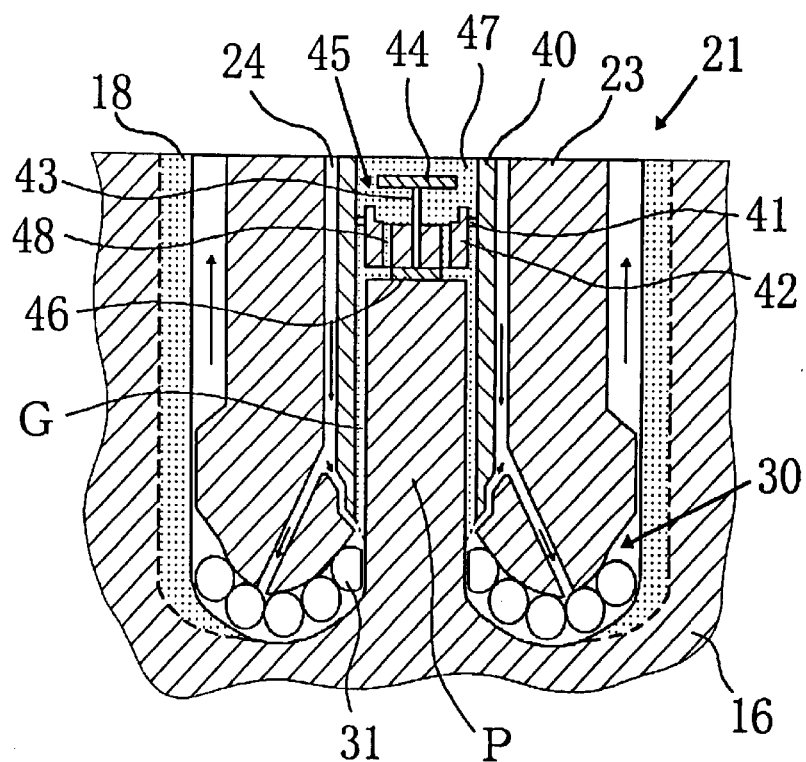
FIG. 5 is a sectional view illustrating the drill pipe and the drill bit during the drilling of the sea bed, with the section taken along the axis of the pipe partly schematically shown.

FIGS. 3 to 5 are sectional views illustrating the states of a drill pipe and a drill bit in a drilling operation as sections. FIG. 3 illustrates the state right before the drilling is started, FIG. 4 the state right after the drilling is started, and FIG. 5 the state that the drilling has been advanced.

In the core sampling system in this embodiment, a pipe-like inner barrel 40 is arranged in an outer barrel 23 constituting the drill pipe 21, and the drill bit 30 is provided on the tip of the outer barrel 23.

In the drill bit 30, a plurality of semi-spherical cutters each projecting downward so as to be arranged in the peripheral direction of the lower end surface of the outer barrel 23 are formed at the lower end surface, and a plurality of cutter elements 31 are fixed to each cutter. The lower end of the inner barrel 40 is constructed so as to have an opening at a position surrounded by the cutters.

The cutter elements 31 of the drill bit 30 are fixed in a state that the innermost peripheral surface of a locus drawn by the rotation thereof is located slightly inside from the inner periphery of the inner barrel 40.

At the lower end of the inner barrel 40, a disk-like gel-ejecting member 42 is arranged in a state that the liquid tightness has been kept so as to close an opening thereof through an ring-like sealing member 41, and movably within and relative to the inner barrel 40 in the vertical directions.

In the gel-ejecting member 42, are formed gel-ejecting orifices 48 vertically extending so as to communicate the interior of the inner barrel 40 with the exterior thereof. Further, an on-off valve mechanism 45 for opening and closing the gel-ejecting member 42 is vertically movably provided. More specifically, the on-off valve mechanism 45 is constructed by a valve member 44 provided on the inner surface side of the gel-ejecting member 42, a connecting rod 43 vertically slidably inserted through the gel-ejecting member 42 and a working disk 46 provided on the lower end of the connecting rod 43 and located on the outer surface side (lower surface side) of the gel-ejecting member 42. The connecting rod 43 has a length greater than the vertical-wise thickness of the gel-ejecting member 42. Antimicrobial polymeric gel (hereinafter referred to as "antimicrobial gel") 47, which will be described subsequently, is filled in the interior of the inner barrel 40.

In such a core sampling system, in the state right before the drilling operation is started, the drill bit 30 does not reach the surface 15 of the crust as illustrated in FIG. 3, so that the connecting rod 43 in the on-off valve mechanism 45 projects from the lower surface of the gel-ejecting member 42, and the valve member 44 is pressed against the upper surface of the gel-ejecting member 42 by the pressure of the antimicrobial gel 47 filled in the interior of the inner barrel 40 to close the gel-ejecting orifices 48. Accordingly, the antimicrobial gel 47 is not ejected outside.

When the drilling of the crust 16 is then started as illustrated in FIG. 4, the outer barrel 23 and the inner barrel 40 go down from the crustal surface 15 with rotating, whereby the working disk 46 provided on the lower end of the connecting rod 43 is pushed upwards by the crustal surface 15, whereby the valve member 44 is detached from the inner surface (upper surface) of the gel-ejecting member 42 through the connecting rod 43 to open the gel-ejecting orifices 48. As a result, the interior of the inner barrel 40 becomes a state communicating with the exterior thereof, so that the antimicrobial gel 47 within the inner barrel 40 is ejected out through the gel-ejecting orifices 48.

As the drilling process is further advanced, the outer barrel 23 and the inner barrel 40 go down with the drilling as illustrated in FIG. 5. However, the on-off valve mechanism 45 is moved upward relative to the inner barrel 40 within the inner barrel 40 while retaining the state that the gel-ejecting orifices 48 in the gel-ejecting member 42 have been communicated.

Since the outer peripheral surface of a column shaped core part P formed by the rotation of the cutter elements 31 in the drill bit 30 is located slightly inside from the inner periphery of the inner barrel 40, a narrow annular space G is defined between the outer peripheral wall surface of the column shaped core part P and the inner peripheral wall surface of the inner barrel 40. As a result, the column shaped core part P is in a state contained in the inner barrel 40 through the annular space G.

In other words, the column shaped core part P being gradually formed by cutting with forming the periphery thereof enters the interior of the inner barrel 40 through the central opening in the drill bit 30 as the outer barrel 23 and the inner barrel 40 are moved downward, relative to the column shaped core part P, with the advance of the drilling.

The column shaped core part P entered in the inner barrel 40 is taken by breaking it, and this broken part is recovered as a crustal core sample together with the inner barrel 40 on the drill ship 10 through the drill pipe 21 by means of a wire or the like.

Figure 6:
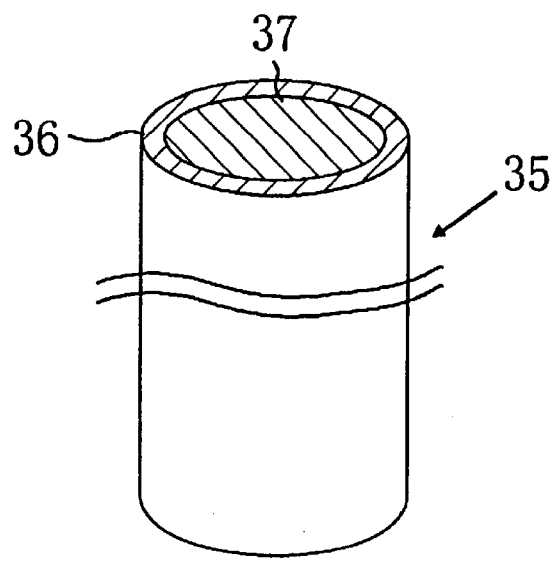
FIG. 6 is a sectional view illustrating a crustal core sample coated with antimicrobial polymeric gel taken perpendicularly to the axis of the barrel.

As described above, the column shaped core part P is gradually formed by drilling by means of the cutters going down. In the course of this drilling, the gel-ejecting member 42 relatively enters within the inner barrel 40 together with the column shaped core part P gradually formed while retaining the state that the gel-ejecting orifices 48 thereof have been communicated by means of the on-off valve mechanism 45. Accordingly, the antimicrobial gel 47 filled in the interior of the inner barrel 40 is ejected in the annular space G through the gel-ejecting orifices 48 and adheres to the outer peripheral surface of the column shaped core part P gradually formed. As illustrated in FIG. 6, a crustal core sample 35 in a state that the outer surface of a crustal core 37 has been coated with antimicrobial gel 36 is formed in such a manner.

Since the antimicrobial gel 47 is fed to the column shaped core part P gradually formed from the upper end thereof in the above-described manner, the antimicrobial gel 47 adhered to the column shaped core part P is substantially not affected by the circulating fluid fed to the drill bit 30 through the inner flow path 24. In addition, the antimicrobial gel 47 also covers the end surface of the column shaped core part P when it is broken out, since the gel has flowability like jam. As a result, the crustal core sample 35 is completely coated with the antimicrobial gel 47.

The present invention has a feature in that antimicrobial gel composed of a polymer obtained by polymerizing an antimicrobial monomer is used in such a method of taking a crustal core sample as described above. The polymer forming this antimicrobial gel is a high-viscosity fluid like jam.

As the antimicrobial monomer for obtaining the polymer forming the antimicrobial gel, is used a compound having a polymerizable functional group having an unsaturated double bond and an antimicrobial atomic group in its molecule. As examples of such a compound, may be mentioned quaternary ammonium salt compounds having an unsaturated double bond and phosphonium salt compounds having an unsaturated double bond.

Specifically, one or more compounds selected from among an aromatic quaternary ammonium salt compound represented by the general formula (1), an acryloyloxyalkyltrialkylammonium salt compound and a methacryloyloxyalkyltrialkylammonium salt compound represented by the following general formula (3), and an aromatic phosphonium salt compound represented by the general formula (2) may preferably be used.

General Formula (3):

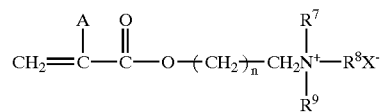

wherein $R^7$, $R^8$ and $R^9$ may be the same or different from one another and independently mean a linear or branched alkyl group having 1 to 16 carbon atoms, $X^-$ denotes a halogen ion, and A represents a hydrogen atom or methyl group.

As specific preferable examples of the antimicrobial monomers, may be mentioned vinylbenzyldimethyl-n-octylammonium salts, vinylbenzyldimethyl-n-decylammonium salts, vinylbenzyldimethyl-n-dodecylammonium salts and vinylbenzyldimethyl-n-hexadecylammonium salts for examples of the antimicrobial monomers represented by the general formula (1).

As examples of the antimicrobial monomers represented by the general formula (2), may be mentioned vinylbenzyltri-n-butylphosphonium salts, vinylbenzyltri-n-octylphosphonium salts, vinylbenzyltri-n-decylphosphonium salts and vinylbenzyltri-n-dodecylphosphonium salts.

As examples of the antimicrobial monomers represented by the general formula (3), may be mentioned 2-acryloyloxyethyltrimethylammonium salts and 2-methacryloyloxyethyltrimethylammonium salts.

As examples of other antimicrobial monomers, may be mentioned acrylamidopropyltrimethylammonium salts, methacrylamidopropyltrimethylammonium salts, acryloyloxyalkylpyridinium salt compounds and methacryloyloxyalkylpyridinium salt compounds.

In the above-described respective compounds, a counter ion is preferably a chloride or bromide ion.

Polymers (including copolymers) obtained by polymerizing the above-described antimicrobial monomers exhibit the antimicrobial effect by the activity of the quaternary ammonium salt structure or phosphonium salt structure contained therein.

When the polymer forming the antimicrobial gel is a copolymer, preference is given in that specific properties can be imparted to the resulting copolymer by selecting the kind of a copolymerizable monomer copolymerized with the antimicrobial monomer.

For example, when a monomer having a hydrophilic group is copolymerized with the antimicrobial monomer, the resulting copolymer has hydrophilicity in itself. When the polymer forming the antimicrobial gel has hydrophilicity, the antimicrobial gel comes to have hydrophilicity. As a result, it is easy to swell with water to easily achieve moderate viscosity. In addition, high affinity is achieved for the crustal core sample, and excellent coating property is hence achieved.

No particular limitation is imposed on the copolymerizable monomer so far as it is copolymerizable with the antimicrobial monomer. However, it is preferable to use one or more of, for example, acrylamide, methacrylamide, N,N-dimethylacrylamide, N-methylacrylamide, N-methylmethacrylamide, N-vinyl-N-methylacetamide, N-isopropylacrylamide, N-(2-hydroxypropyl)acrylamide, N-(2-hydroxypropyl)methacrylamide, N,N-dimethyl methacrylamide, 2-hydroxyethyl acrylate, 2-hydroxyethyl methacrylate, hydroxypropyl acrylate, hydroxypropyl methacrylate, 4-hydroxybutyl acrylate, 4-hydroxybutyl methacrylate, N-acryloyltris(hydroxymethyl)methylamine, N-methacryloyltris(hydroxymethyl)methylamine, vinylpyrrolidone and N-acryloyl-morpholine, N-methacryloyl-morpholine in that the resulting copolymer becomes hydrophilic.

A crosslinkable monomer may be used as the whole or a part of the copolymerizable monomer. As the crosslinkable monomer, may preferably be used one or more of, for example, N,N'-methylenebisacrylamide, diethylene glycol diacrylate, diethylene glycol dimethacrylate, diethylene glycol divinyl ether, poly(ethylene glycol) dimethacrylate, poly(ethylene glycol) diacrylate, poly(ethylene glycol) dimethacrylate, poly(ethylene glycol) diacrylate and poly(propylene glycol) dimethacrylate.

When the polymer forming the antimicrobial gel is a copolymer, the copolymer preferably contains the component of the antimicrobial monomer in a proportion of 1 to 10 mol %, particularly 3 to 8 mol %.

No particular limitation is imposed on the process for obtaining the polymer forming the antimicrobial gel, and a polymerization process generally used, specifically, a radical polymerization reaction using a radical polymerization initiator may be utilized.

As the radical polymerization initiator, any radical polymerization initiator may be used without particular limitation so far as it is a generally used. As examples thereof, may be mentioned hydrogen peroxide, ammonium persulfate, potassium persulfate, t-butyl hydroperoxide, azobisisobutyronitrile, 2,2'-azobis-(2-methylpropionamide) dihydrochloride, 2,2'-azobis-[2-(2-imidazolin-2-yl)propane] dihydrochloride and 2,2'-azobis(2-amidinopropane) dihydrochloride. In addition, publicly known redox initiators, for example, hydrogen peroxide and ferrous sulfate, and potassium persulfate and sodium hydrogensulfite may also be used.

As a solvent used in the polymerization reaction, may be used water, a mixed solvent of water and a water-soluble organic solvent, etc. As specific examples of the water-soluble organic solvent, may be mentioned alcohols such as methanol, ethanol, isopropanol and n-propanol, amide compounds such as formamide and dimethylformamide, and polar solvents such as tetrahydro furan, aceton, dioxane, acetonitrile and dimethyl sulfoxide.

The polymerization reaction is only required to conduct the reaction at a temperature and for a period of time according to the kinds of the monomer(s) and radical polymerization initiator used and other conditions. For example, the polymerization reaction is conducted at a temperature of about 50 to 90° C. for about 3 to 24 hours. In this polymerization reaction, it is necessary to conduct the reaction under an inert gas atmosphere with, for example, nitrogen gas.

The polymer of the antimicrobial monomer permits providing antimicrobial gel, which is a jam-like fluid having suitable viscosity, by swelling it with water.

In the present invention, the antimicrobial gel preferably has a viscosity of 8.0×30.0 Nsm$^{-2}$, particularly 8.5 to 24.0 Nsm$^{-2}$ as measured at normal temperature and a shear rate of 6.8 to 17 sec$^{-1}$.

The antimicrobial gel used in the present invention can be generally provided as a dry powdered material by conducting proper means, for example, a dehydration treatment. This powdered gel material is extremely useful in that it is easy to ship and store because the weight is greatly reduced, and moreover it can be restored to gel by bringing it into simply contact with water to make it a swollen state to provide an antimicrobial gel. More specifically, when the powdered gel material is used, required antimicrobial gel can be prepared with ease by an operation of only addition of water in a drilling site, and moreover antimicrobial gel in a viscous state suitable for the geology of the crust drilled can be provided by controlling the amount of water added.

According to such antimicrobial gel as described above, an excellent antimicrobial performance is achieved by containing the antimicrobial component composed of the antimicrobial monomer, and moreover the antimicrobial component is prevented from being separated and dissolved out to the exterior, since the antimicrobial component forms a part of the molecular structure of the polymer. Accordingly, the crustal core sample taken is not contaminated with the antimicrobial component, and so the ecological system of said crustal core sample is sufficiently protected, and moreover the antimicrobial activity or antimicrobial action of the antimicrobial polymeric gel is exhibited stably over a long period of time.

In addition, the antimicrobial gel itself is prevented from becoming a contamination source of microbial contamination against the crustal core sample because growth of microorganisms within the antimicrobial gel is prohibited.

The drilling methods in the case where the method of coring a crustal core sample according to the present invention is practiced are not limited to specific methods, and this method can be applied to publicly known various drilling methods. In particular, the method can be easily practiced in the drilling of the submarine crust making good use of a drill ship such as the above-described riser drilling method.

Although the method of taking a crustal core sample according to the present invention has been described specifically above, various modifications may be made in the present invention.

Preparation Example 1:
Preparation of Antimicrobial Monomer

A 100-ml four-necked flask equipped with a dropping funnel, a stirrer and a temperature sensor was charged with 7.63 g (0.05 mol) of chloromethyl-styrene and 50 ml of n-hexane. 16.17 g (0.06 mol) of dimethyl-n-hexadecylamine was added dropwise from the dropping funnel over 30 minutes while stirring the contents at 25° C. After the resultant solution was stirred at 25° C. for 8 hours, deposits were collected by filtration, washed with n-hexane and diethyl ether and then dried, thereby obtaining vinylbenzyldimethyl-n-hexadecylammonium chloride having an unsaturated double bond which is a white solid quaternary ammonium salt compound.

Copolymerization Reaction

A pressure bottle, which was a reactor, was charged with 23.6 g (665 mM) of acrylamide and 0.65 g (8.4 mM) of N,N'-methylenebisacrylamide, which were copolymerizable comonomers, 0.24 g (1.8 mM) of 2,2'-azobis(2-amidinopropane) dihydrochloride and 7.4 g (35 mM) of vinylbenzyldimethyl-n-hexadecylammonium chloride obtained in Preparation Example 1, which was an antimicrobial monomer, together with 500 ml of purified water which was a polymerization reaction solvent. After internal air was purged with nitrogen gas for 30 minutes, the pressure bottle containing the polymerization reaction solution was placed in an incubator controlled at 70° C. to conduct a polymerization reaction treatment.

The resultant polymer was taken out of the pressure bottle and immersed in distilled water to remove unreacted residual monomers, and a solid copolymer thus obtained was ground to obtain Sample 1.

Preparation Examples 2 to 5:
Antimicrobial monomers were obtained in the same manner as in preparation Example 1 except that various amine compounds were used in place of dimethyl-n-hexadecylamine in the preparation of the antimicrobial monomer in Preparation Example 1.

More specifically, dimethyl-n-octylamine was used in Preparation Example 2 to prepare vinylbenzyldimethyl-n-octylammonium chloride which was an antimicrobial monomer, dimethyl-n-decylamine was used in Preparation Example 3 to prepare vinylbenzyldimethyl-n-decylammonium chloride, dimethyl-n-dodecylamine was used in Preparation Example 4 to prepare vinylbenzyldimethyl-n-dodecylammonium chloride, and dimethyl-n-tetradecylamine was used in Preparation Example 5 to prepare vinylbenzyldimethyl-n-tetradecylammonium chloride.

The antimicrobial monomers obtained in Preparation Examples 2 to 5 were respectively used to conduct a copolymerization reaction in the same manner as in preparation Example 1, thereby obtaining copolymers. These copolymers were regarded as Samples 2 to 5, respectively.

Preparation Examples 6 and 7:

In Preparation Examples 6 and 7, 2-acryloyloxyethyltrimethylammonium chloride (product of Polyscience Co.) and tributyl-4-vinylbenzyl-phosphonium chloride (product of Nippon Chemical Industrial Co., Ltd.) were respectively used as antimicrobial monomers to conduct a copolymerization reaction in the same manner as in Preparation Example 1, thereby obtaining copolymers. They were regarded as Samples 6 and 7, respectively.

Preparation Example of Comparative Standard Sample:

A pressure bottle, which was a reactor, was charged with 24.9 g (700 mM) of acrylamide, 0.65 g (8.4 mM) of N,N'-methylenebisacrylamide and 0.24 g (1.8 mM) of 2,2'-azobis(2-amidinopropane) dihydrochloride together with 500 ml of purified water which was a polymerization reaction solvent. After internal air was purged with nitrogen gas for 30 minutes, the pressure bottle containing the polymerization reaction solution was placed in an incubator controlled at 70° C. to conduct a polymerization reaction treatment.

The resultant polymer was taken out of the pressure bottle and immersed in distilled water to remove unreacted residual monomers, and a solid copolymer thus obtained was ground to obtain a comparative standard sample.

Experimental Example 1:

Evaluation of Antimicrobial Activity on Gel Surface

Each of microorganisms shown in Table 1 was added to and dispersed in physiological saline in such a manner that the number of cells was $1 \times 10^5$ cells/ml, and the resultant cell solution was spread onto an agar plate containing no medium component.

However, when the microorganisms were *Streptomyces albus* (IFO 13014) and *Aspergillus terreus* (IFO 6346), it was difficult to prepared physiological saline in which cells were evenly dispersed. Therefore, the cells were planted onto each agar plate by means of a toothpick.

Each of antimicrobial gel samples obtained from Samples 1 to 7 in Preparation Examples 1 to 7, and the comparative standard sample was laid on the cell solution spread on the agar plate to leave it to stand at room temperature for 3 hours.

Incidentally, the antimicrobial monomer is contained in a proportion of 5 mol % in each of the antimicrobial gel in the above-described experiment.

The microorganisms used are as follows:

TABLE 1

| No. | Microorganism Name | |
|---|---|---|
| 1 | *Escherichia coli* | ATCC 12435 |
| 2 | *Pseudomonas aeruginosa* | IFO 13275 |
| 3 | *Vibrio diazotrophicus* | DSM 2604 |
| 4 | *Cytophaga marinoflava* | JCM 8517 |
| 5 | *Photobacterium phosphoreum* | ATCC 11040 |
| 6 | *Shewanella putrefaciens* | IAM 12079 |
| 7 | *Bacillus subtilis* | JCM 1465 |
| 8 | *Planococcus citreus* | IFO 15849 |
| 9 | *Arthrobacter globiformis* | JCM 1332 |
| 10 | *Staphylococcus condimenti* | JCM 6074 |
| 11 | *Streptomyces albus* | IFO 13014 |
| 12 | *Saccharomyces cerevisiae* | IFO 10217 |
| 13 | *Aspergillus terreus* | IFO 6346 |

Thereafter, a medium component was added to the respective antimicrobial gel samples and comparative standard sample to conduct culture at a temperature for optimum growth of each microorganism for 24 hours for *Escherichia coli* and *Pseudomonas aeruginosa*, for 48 hours for *bacillus subtilis* and *Aspergillus terreus* and for 72 hours for other microorganisms than these.

After the culture, the number of colonies formed per unit area on the agar plate brought into contact with each of the respective samples and comparative standard sample was counted to conduct evaluation. More specifically, each sample was ranked as "Excellent" where the survival rate A calculated out in accordance with the following equation 1 was lower than 1%, as "Good" where the survival rate A was 1 to 10%, or as "Poor" where the survival rate A was higher than 10%. The results of the evaluation on the respective Samples 1 to 7 are shown in Table 2. In the table 1, "Excellent" is notated as "E", "Good" is notated as "G", "Poor" is notated as "P".

However, when the microorganisms were *Streptomyces albus* and *Aspergillus terreus*, each sample was ranked as "Excellent" where any colony was clearly not formed on the agar plate brought into contact with each antimicrobial gel, or as "Poor" in any other case.

The survival rate A is calculated out in accordance with the following equation 1:

Survival rate A (%)=(Number of colonies formed per unit area on the agar plate brought into contact with antimicrobial gel/Number of colonies formed per unit area on the agar plate brought into contact with the comparative standard sample)× 100    Equation 1:

Experimental Example 2:

Evaluation of Antimicrobial Effect of Gel on Permeation of Adventitious Heterogeneous Microorganisms Each of Samples 1 to 7 and the comparative standard sample was packed on the bottom part of a column having an inner diameter of 15 mm so as to give a thickness of 10 mm.

A cell solution obtained by adding and dispersing each of the microorganisms shown in Table 1 in physiological saline in such a manner that the number of cells was $1 \times 10^7$ cells/ml was added in an amount of 5 ml to the column, and the column was left to stand at room temperature. With respect to *Streptomyces albus* and *Aspergillus terreus*, a supernatant solution obtained by adding each cultured cell strain to physiological saline, vigorously stirring the mixture and subjecting the mixture to a centrifugal treatment was used. Thereafter, the physiological saline fallen from the bottom of column was collected and spread onto an agar medium. Since no falling of the physiological saline was observed on the comparative standard sample, physiological saline before passed through the antimicrobial gel was spread onto an agar medium for comparison. Culture was then conducted at a temperature for optimum growth of each microorganism, and the number of colonies formed are counted, thereby ranking each gel sample as "Excellent" where the survival rate B calculated out in accordance with the following equation 2 was lower than 1%, as "Good" where the survival rate B was 1 to 10%, or as "Poor" where the survival rate B was higher than 10%. The results of the evaluation on the respective Samples 1 to 7 are shown in Table 2. In the table 2, "Excellent" is notated as "E", "Good" is notated as "G", "Poor" is notated as "P".

However, when the microorganisms were *Streptomyces albus* and *Aspergillus terreus*, each sample was ranked as "Excellent" where any colony was clearly not formed on the agar medium, or as "Poor" in any other case.

number of colonies formed on the surface of each crustal core sample to rank each gel sample as "Excellent" where the survival rate C calculated out in accordance with the following equation 3 was lower than 1%, as "Good" where the survival rate C was 1 to 10%, or as "Poor" where the survival rate C was higher than 10%. The results of the evaluation on the respective Samples 1 to 7 are shown in Table 3. In the table 3, "Excellent" is notated as "E", "Good" is notated as "G", "Poor" is notated as "P".

The survival rate C is calculated out in accordance with the following equation 3:

Survival rate C (%)=(Number of colonies formed per unit area on the crustal core sample coated with the antimicrobial gel/Number of colonies formed per unit area on the crustal core sample coated with the comparative standard sample)×100  Equation 3:

TABLE 2

| Micro-organism No. | Antimicrobial Monmer | | | | | | | | | | | | |
|---|---|---|---|---|---|---|---|---|---|---|---|---|---|
| | Sample 1 | | Sample 2 | | Sample 3 | | Sample 4 | | Sample 5 | | Sample 6 | | Sample 7 |
| | A | B | A | B | A | B | A | B | A | B | A | B | A | B |
| 1 | G | E | G | E | E | E | E | E | E | E | G | E | G | E |
| 2 | E | E | G | E | G | E | E | E | G | E | G | E | G | E |
| 3 | E | E | E | E | E | E | G | E | E | E | G | E | G | E |
| 4 | E | E | E | E | E | E | E | E | E | E | E | E | E | E |
| 5 | E | E | E | E | E | E | E | E | E | E | E | E | E | E |
| 6 | E | E | E | E | E | E | E | E | E | E | E | E | E | E |
| 7 | E | E | G | E | G | E | G | E | E | E | G | E | G | E |
| 8 | E | E | E | E | E | E | E | E | E | E | E | E | E | E |
| 9 | E | E | E | E | E | E | E | E | E | E | E | E | E | E |
| 10 | E | E | E | E | E | E | E | E | E | E | E | E | E | E |
| 11 | E | E | G | E | G | E | E | E | E | E | P | E | P | E |
| 12 | E | E | G | E | G | E | E | E | E | E | G | E | G | E |
| 13 | E | E | G | E | G | E | E | E | E | E | P | E | P | E |

The survival rate B is calculated out in accordance with the following equation 2:

Survival rate B (%)=(Number of colonies formed from the physiological saline passed through the antimicrobial gel/Number of colonies formed from the physiological saline before passed through the antimicrobial gel)×100  Equation 2:

In Table 2 shown above, columns A are columns showing the evaluation of the antimicrobial activity on the gel surface, and columns B are columns showing the evaluation of the antimicrobial effect of gel on permeation of adventitious heterogeneous microorganisms.

TABLE 3

| Experimental Example | Antimicrobial Monmer | | | | | | |
|---|---|---|---|---|---|---|---|
| | Sample 1 | Sample 2 | Sample 3 | Sample 4 | Sample 5 | Sample 6 | Sample 7 |
| Evaluation of antimicrobial activity of gel using crustal core sample | E | G | E | E | E | G | G |

Experimental Example 3:
Evaluation of Antimicrobial Activity of Gel Using Crustal Core Sample Crustal core samples taken by drilling the crust and respectively coated with antimicrobial gel samples obtained from Samples 1 to 7 and the comparative standard sample were left to stand at room temperature for 3 hours.

A medium was penetrated into the coating layers formed respectively of the antimicrobial gel samples and the comparative standard sample from the outside to conduct culture at room temperature for 72 hours, thereby counting the As apparent from the results shown in Tables 2 and 3, the antimicrobial gel of Samples 1 to 7 exhibit excellent antimicrobial effects on various kinds of microorganisms. Accordingly, these antimicrobial gel are used for coating crustal core samples in the method of taking the crustal core samples, whereby the crustal core samples can be taken in a state free of any microbial contamination. These crustal core samples are suitable for use in researches on intracrustal microorganisms.

What is claimed is:

1. A method of taking a crustal core sample, comprising drilling the crust, wherein the crustal core sample is taken in a state coated with an antimicrobial polymeric gel formed of a polymer obtained by polymerizing an antimicrobial monomer.

2. The method according to claim 1, wherein the antimicrobial monomer used for obtaining the polymer forming the antimicrobial polymeric gel is a quaternary ammonium salt compound.

3. The method according to claim 2, wherein the quaternary ammonium salt compound is at least one compound selected from the group consisting of an aromatic compound represented by the following formula (1), an acryloyloxyalkyltrialkylammonium salt compound, a methacryloyloxyalkyltrialkylammonium salt compound, an acryloyloxyalkylpyridinium salt compound and a methacryloyloxyalkylpyridinium salt compound; wherein the formula (1) comprises:

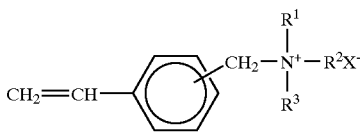

(1)

wherein $R^1$ means a linear or branched alkyl group having 1 to 18 carbon atoms, $R^2$ and $R^3$ are methyl groups, and $X^-$ denotes a halogen ion.

4. The method according to claim 3, wherein the compound of the formula (1) is selected from the group consisting of a vinylbenzyldimethyl-n-octylammonium salt, a vinylbenzyl-dimethyl-n-decylammonium salt, a vinylbenzyl-dimethyl-n-dodecylammonium salt and a vinylbenzyl-dimethyl-n-hexadecylammonium salt.

5. The method according to claim 1, wherein the antimicrobial monomer used for obtaining the polymer forming the antimicrobial polymeric gel is a phosphonium salt compound.

6. The method according to claim 5, wherein the phosphonium salt compound is an aromatic compound represented by the following formula (2):

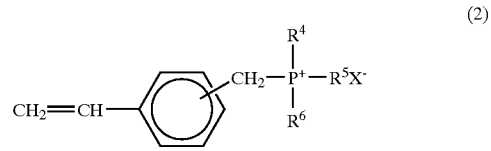

(2)

wherein $R^4$, $R^5$ and $R^6$ are the same or different from one another and independently mean a linear or branched alkyl group having 1 to 18 carbon atoms, and $X^-$ denotes a halogen ion.

7. The method according to any one of claims 1 to 6, wherein the polymer forming the antimicrobial polymeric gel contains a component derived from the antimicrobial monomer in a proportion of 1 to 10 mol %.

8. The method according to any one of claims 1 to 7, wherein the polymer forming the antimicrobial polymeric gel is hydrophilic.

9. The method according to claim 8, wherein the polymer forming the antimicrobial polymeric gel is a copolymer obtained from the antimicrobial monomer and at least one compound selected from the group consisting of acrylamide, methacrylamide, N,N'-methylenebisacrylamide and N,N'-methylenebismethacrylamide.

10. The method according to claim 6, wherein the compound of the formula (2) is selected from the group consisting of a vinylbenzyltri-n-butylphosphonium salt, a vinylbenzyltri-n-octylphosphonium salt, a vinylbenzyltri-n-decylphosphonium salt and a vinybenzyltri-n-dodecylphosphonium salt.

* * * * *